United States Patent [19]

Tive

[11] Patent Number: 5,280,809
[45] Date of Patent: Jan. 25, 1994

[54] MEDICAL CONDUIT END BREATHER CAP

[75] Inventor: Bruce E. Tive, Westminster, Colo.

[73] Assignee: Cobe Laboratories, Inc., Lakewood, Colo.

[21] Appl. No.: 952,301

[22] Filed: Sep. 28, 1992

Related U.S. Application Data

[63] Continuation of Ser. No. 374,176, Jun. 30, 1989, abandoned.

[51] Int. Cl.⁵ .............. F61L 55/10; A61M 1/00; A61M 25/00; A61B 19/02
[52] U.S. Cl. .................. 138/89.3; 138/89; 138/89.2; 138/96.0012; 206/363; 206/364; 220/352; 220/356; 220/367; 215/307; 215/317; 215/320
[58] Field of Search .......... 138/39, 89.3, 40, 89, 138/96 R, 96 T, 89.2; 206/363, 364, 306, 438, 210, 205, 303; 220/356, 360–367, 374, 352; 215/307, 317, 320; 55/316; 604/256

[56] References Cited

U.S. PATENT DOCUMENTS

| | | | |
|---|---|---|---|
| 1,307,947 | 6/1919 | Williams | 138/89.2 |
| 1,556,966 | 10/1925 | Selig | 138/96.12 |
| 2,841,166 | 7/1958 | Auzin | 215/307 |
| 3,297,184 | 1/1967 | Andelin | 215/307 |
| 3,437,224 | 4/1969 | Williams | 215/307 |
| 3,589,368 | 6/1971 | Jackson | 138/89 |
| 3,606,001 | 9/1971 | Talonn et al. | 220/356 |
| 3,921,845 | 11/1975 | Vogel, Jr. | 215/320 |
| 4,190,087 | 2/1980 | Herman et al. | 138/96.12 |
| 4,335,756 | 6/1982 | Sharp et al. | 138/96.12 |
| 4,411,163 | 10/1983 | White | 215/309 |
| 4,427,126 | 1/1984 | Ostrowsky | 215/307 |
| 4,597,758 | 7/1986 | Aalto et al. | |

*Primary Examiner*—Timothy F. Simone
*Assistant Examiner*—Gary K. Graham

[57] ABSTRACT

A breather cap for protecting the ends of tubing and barbed connectors during sterilization and until use in which interference is at a detent spaced from the conduit end, or a positive stop is provided for the conduit end, or a flat handle is provided to facilitate removal of cap from conduit, or two or all of these features are present.

1 Claim, 1 Drawing Sheet

MEDICAL CONDUIT END BREATHER CAP

This application is a continuation of application Ser. No. 374,176, filed Jun. 30, 1989, now abandoned.

FIELD OF THE INVENTION

This invention relates to breather caps for use in sterilizing and keeping sterile the ends of conduits such as plastic barbed connectors and tubing.

BACKGROUND OF THE INVENTION

It is known in the prior art to provide breather caps (protector caps) on the ends of plastic tubing and barbed connectors during sterilization, in breather bags, of packs containing them. Such caps include a multiplicity of circumferentially spaced passages around the tapered inner surface for cooperation with a tubing or connector end portion to permit sterilant to move over the connector end during bag sterilization; these prior art devices included a reduced diameter end portion, circular in cross-section, inside diameter being reduced gradually through a portion between the tapered portion and the reduced diameter portion.

SUMMARY OF THE INVENTION

It has been discovered that an improved breather cap is provided if the interference fit provided for is at a detent spaced from the end of the connector or other conduit member fitted therein. It has been further discovered that a breather cap is desirably provided with a positive conduit member end stop. It has also been discovered that a breather cap is desirably furnished with a flattened portion, at its end away from the conduit member, the flattened portion being of area to facilitate gripping and removal of the breather cap.

PREFERRED EMBODIMENT

We turn now to the presently preferred embodiment.

DRAWINGS

STRUCTURE

Figure 1:
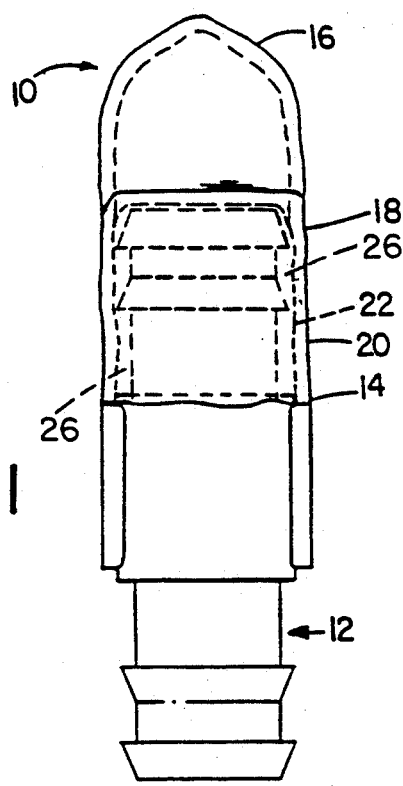
FIG. 1 is a plan view of said embodiment, mounted on a barbed plastic connector.
Figure 3:
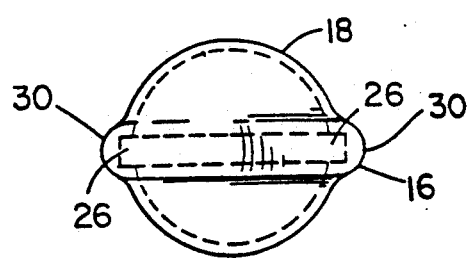
FIG. 3 is an end elevation view thereof.
Figure 4:
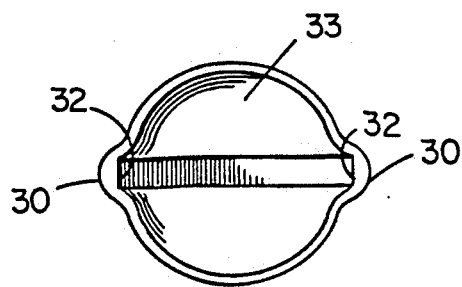
FIG. 4 is an end elevation view of said embodiment, looking into the open end thereof.
Figure 2:
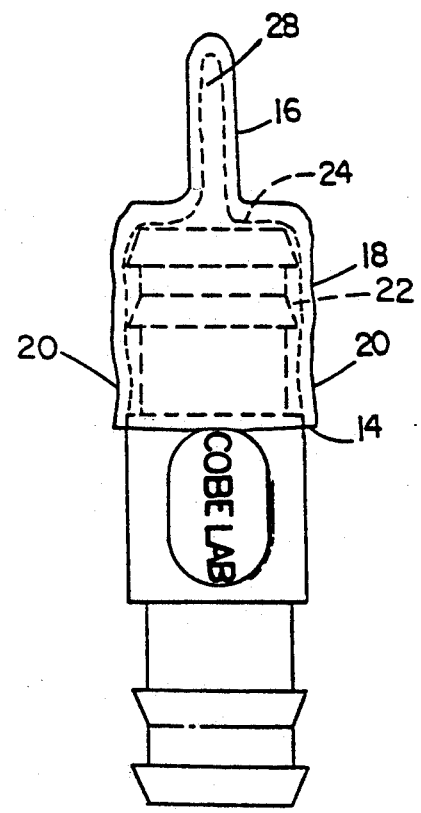
FIG. 2 is a side elevation view thereof.

There is shown in the drawings a breather cap indicated generally at 10, molded of a flexible plastic material of approximately uniform wall thickness formed from plastisol (liquid highly DOP-plasticized PVC) as well known in the art (0.050 inches), shown mounted on a barbed connector, indicated generally at 12.

Cap 10, which is elongated, hollow, and unitary, with tow end and a central longitudinal axis, and defining a closed region open only at the circular opening 33, and includes open-end conduit portion 14A circular in transverse cross-section and defining a circular opening 33 at its outermost extend, closed end conduit portion 16, and intermediate portion 18.

Adjacent open end portion 14 is detent portion 20 generally circular in transverse cross-section adjacent circular opening 33, the surface of which is generally arcuate, except passage zone portions, when cut by planes in which lie the axis of the cap 10. The center of the detent is spaced from the open end, and said "arc" extends thereto. A parallel arc isosimilarly defined (by a plane including the cap axis) on the inner surface 22. The detent portion thus has an inner surface with radii smaller than the radius of curvature of circular opening 33, the detent portion thus having a minimum radius of curvature spaced from the circular opening 33.

Inner walls 22, from detent 20 to conduit stop means 24, are cylindrical. Passageways 26 are defined by the conduit outer wall, on the inside, and by the inner surfaces 32 of the two ribs 30, on the outside, to provide channels on the inside surface extending between circular opening 33 and the open zone.

Outer end portion 16 has two spaced-apart walls defining an open zone generally rectangular in transverse cross-section includes open zone 28 and is of transverse width and length sufficient to provide for reliably grasping the cap to remove it from a conduit member.

OPERATION

In use, cap 10 may be slipped over conduit ends, for example of plastic tubing or barbed connectors, in a medical conduit assembly or pack, the whole put into a breather bag, and the latter then put through airwash cycles (alternating evacuation and pressure introduction of ethylene oxide, all as known in the art) through a vapor-permeable bag portion. During this operation, passages 26 provide for gas passage for sterilization of conduit end portions.

When the user ultimately breaks open the bag for use, cap 10 protects against inadvertent loss of sterilization prior to assembly of the tubing or barbed connector to the device with which it is to be used.

Spacing the interfering portion of the cap from the end of the conduit not only gives more reliable retention, but prevents injury to conduit ends during sterilization. The stop 24 provides for easier and more accurate assembly of caps onto conduits. In removal, the "duckbill" end portion 16 and ribs 30 allow opening up increased diameters, so that forces on the conduit are minimized, and shear of plastic by barbs prevented. The duckbill provides a good handle for removal of even wet and slippery caps.

What is claimed is:

1. A breather cap for attachment to an end of a conduit being sterilized, said cap comprising an elongated, hollow, unitary member of flexible plastic having a central longitudinal axis and defining two ends, said member having an open end conduit portion at one end which is circular in transverse cross-section, said open end conduit portion defining a circular opening with an inner diameter at its outermost extent, said unitary member defining a closed region open only at said circular opening, said other end of said unitary member having a closed end conduit portion having two spaced-apart walls defining an open zone that is generally rectangular in transverse cross-section, conduit stop means located intermediate said open end portion and said closed end portion for restraining conduit movement in said cap, said open end conduit portion including a detent portion generally circular in transverse cross-section located adjacent said circular opening, said detent portion having an inner surface that has radii of curvature about said central longitudinal axis, said radii being smaller than the radius of curvature of said circular opening, said detent portion having a minimum radius of curvature spaced from said circular opening, and said member having channels on the inside surface extending between said circular opening and said open zone to provide for fluid flow between said circular opening and said open zone when said cap is attached to an end of a conduit.

* * * * *